United States Patent [19]
Glatz et al.

[11] Patent Number: 5,538,538
[45] Date of Patent: Jul. 23, 1996

[54] METHOD FOR THE MANUFACTURE OF PLASTIC PARTS

[75] Inventors: Bernd Glatz, Leonberg; Manfred Berndt, Waldbronn, both of Germany

[73] Assignee: Hewlett-Packard Company, Palo Alto, Calif.

[21] Appl. No.: 261,892

[22] Filed: Jun. 15, 1994

[30] Foreign Application Priority Data

Aug. 17, 1993 [DE] Germany .................. 43 27 582.6

[51] Int. Cl.⁶ ........................................... B01D 19/00
[52] U.S. Cl. .................. 96/6; 95/46; 96/10; 134/10; 264/39; 264/127; 264/211
[58] Field of Search ................... 264/127, 211, 264/39, 169; 208/89; 134/10; 55/159; 96/6, 10, 193, 101; 95/46, 82

[56] References Cited

U.S. PATENT DOCUMENTS

| | | | |
|---|---|---|---|
| 3,856,686 | 12/1974 | Sato et al. | 252/30 |
| 4,096,227 | 6/1978 | Gore | 264/127 |
| 4,362,069 | 12/1982 | Giatras et al. | 264/127 |
| 4,469,495 | 9/1984 | Hiraizumi et al. | |
| 4,518,485 | 5/1985 | LaPierre | 208/89 |
| 4,729,773 | 3/1988 | Shirato et al. | |
| 4,826,725 | 5/1989 | Harlow | 264/127 |
| 4,902,423 | 2/1990 | Bacino | 210/500.36 |
| 4,913,797 | 4/1990 | Albinson et al. | 208/89 |
| 5,096,501 | 3/1992 | Dishart et al. | 134/10 |
| 5,183,486 | 2/1993 | Gatten et al. | 55/159 |
| 5,269,836 | 12/1993 | Johannes et al. | 96/6 |
| 5,433,909 | 7/1995 | Martakos et al. | 264/127 |

*Primary Examiner*—Jeffery R. Thurlow

[57] ABSTRACT

In a method for the manufacture of plastic parts which are used in an analytical measuring device and there come into contact with liquids, plastic base material is mixed with a suspension liquid and then extruded in the form desired. Before it is mixed with the plastic base material, aromatic and olefinic substances are removed from the suspension liquid by means of a chemical reaction, for instance, so that the final plastic products are free from such substances. In that way, it is avoided that, when using the plastic parts in an analytical measuring device, it may come to interferences of the detection by extraction of such substances into the flow of liquids and transportation into the detector. A vacuum degasser is a particularly advantageous field of application for the plastic parts manufactured in accordance with the invention.

21 Claims, 1 Drawing Sheet

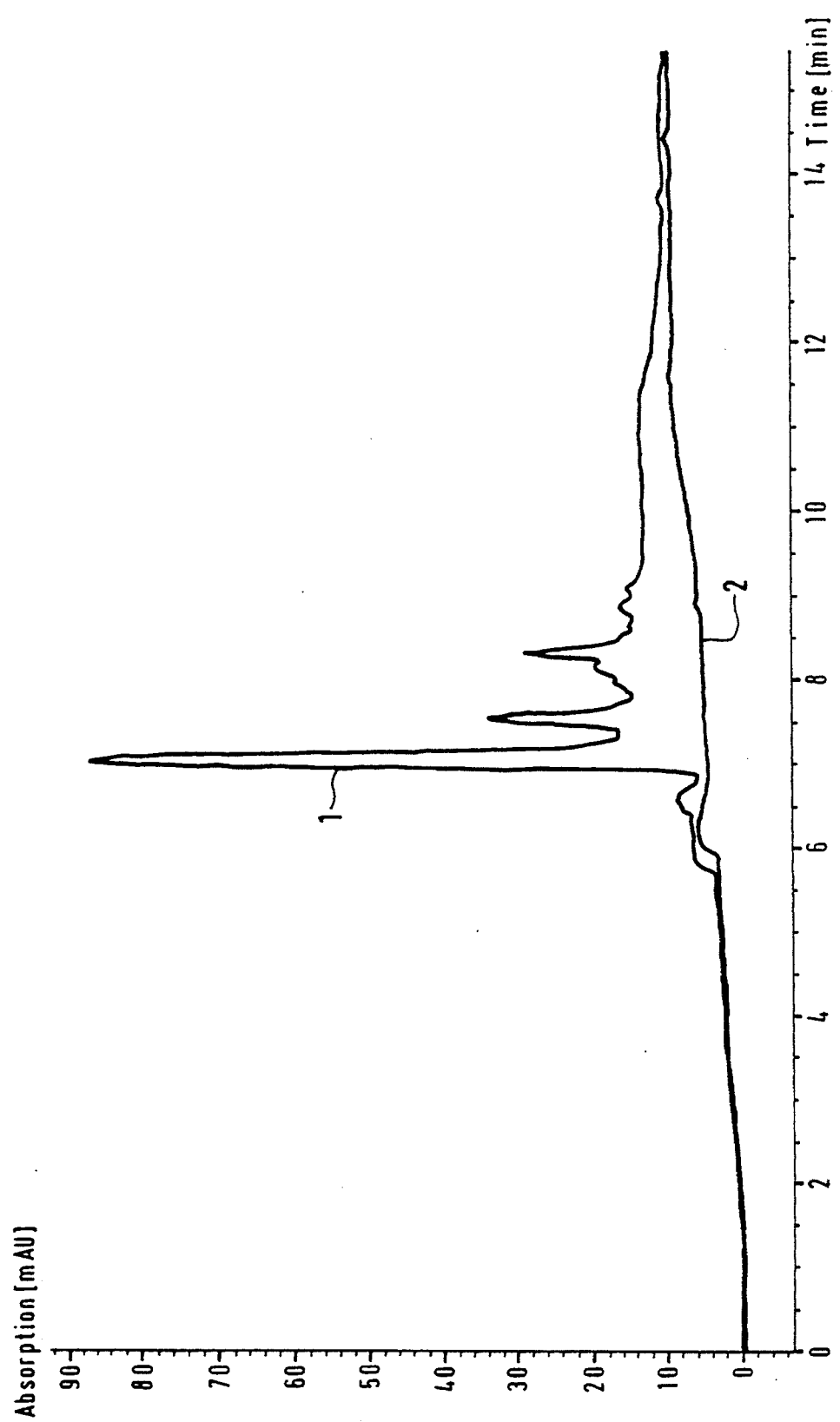

METHOD FOR THE MANUFACTURE OF PLASTIC PARTS

TECHNICAL FIELD

The invention relates to a method for the manufacture of plastic parts in accordance with the invention claimed and the use of a plastic part manufactured in this way in an analytical measuring device, for example in the degasser of a liquid chromatograph.

BACKGROUND

Analytical measuring devices frequently use plastic parts which come into contact with the liquids used in the measuring device, such as the sample liquid, solvent or buffer solution. Polytetrafluoroethylene (PTFE) tubes, which may be used in a liquid chromatograph or in a capillary electrophoresis device for the transport of liquids, may be mentioned as examples of this.

DISCLOSURE OF THE INVENTION

PTFE tubes are particularly used in the degassers of liquid chromatographs. In these devices, the solvent (mobile phase) to be degassed flows through one or more PTFE tubes arranged in parallel and subject to an external vacuum. The PTFE material is permeable to gases, but not to liquids, so that gases can diffuse through the PTFE, whilst the solvent is retained. Degassers of this type are particularly suitable for on-line degassing of solvents. Degassers of the type described are known, for instance, from U.S. Pat. No. 4,469,495 and U.S. Pat. No. 4,729,773.

PTFE tubes, films and membranes are normally manufactured by an extrusion process. In this process, PTFE powder is mixed to a paste with suspension liquid, in this case a gasoline fraction, extruded and then sintered at high temperatures (approximately 150–400 degrees Celsius). The low boiling liquid evaporates during sintering.

In accordance with the present invention, it was surprisingly discovered that the gasoline fraction does not evaporate completely, in contradiction of the usual assumptions, and that a small residue, in particular consisting of aromatic and/or olefinic substances, remains. When liquids, for instance solvents in liquid chromatography, come into contact with plastic parts manufactured by this method, substances may be extracted which are detected by the downstream detector in the analytical measuring device and falsify the measuring signals. Where degassers of the nature mentioned above are used, the surface area of the PTFE tube and thus the contact area with the solvent is particularly great, and so the problems of contamination are particularly significant here. Aromatic and olefinic substances passing into a UV absorption detector through the solvent in this way, lead to an additional absorption signal which interferes with the measuring signal. Contaminations are particularly concentrated in gradient elution in liquid chromatography, thereby exacerbating the problem even further.

The basic object of the present invention is to substantially prevent the mentioned interferences in the detection in analytical measuring devices.

This object is solved by the features of the invention claimed. A significant contribution to the invention can be seen in the fact that the problems of contamination were detected in the first place. In accordance with the invention, the problem of contamination is solved in that the aromatic and/or olefinic substances are removed from the suspension liquid (e.g., the gasoline fraction) used to create the plastic paste to be extruded in the manufacture of the plastic parts referred to. In this way, a plastic part is manufactured which will not release any interfering substances which could interfere with detection, even in intensive contact with the liquids used in an analytical device. A particularly advantageous application of a plastic part manufactured in accordance with the invention, such as a tube or membrane, is in an on-line vacuum degasser.

DESCRIPTION OF THE INVENTION

In a preferred example embodiment of the invention, the aromatic and olefinic constituents are removed from the suspension liquid used in the manufacture of the plastic parts by means of a chemical reaction. This can be carried out, for example, by adding chlorosulphuric acid to the liquid.

The invention gives an effective opportunity for the simple manufacture of plastic parts which will not lead to corruption of the measurement when used in analytical devices. An important characteristic of the invention is that the aromatic or olefinic constituents are removed from the suspension liquid before the plastic parts are actually formed. It has surprisingly been discovered that cleaning the finished plastic parts by processes such as extraction or heat treatment in a high vacuum does not satisfactorily remove the contaminations.

An embodiment of the invention will be described below on the basis of the FIGURE.

BRIEF DESCRIPTION OF THE DRAWING

The FIGURE shows a comparison of two chromatograms to illustrate the problems of contamination solved by the invention.

A preferred field of application for the invention is the manufacture of PTFE tubes for use in a vacuum degasser of the initially mentioned type. In the manufacturing process of these tubes, PTFE powder is mixed with a gasoline fraction to produce a paste, which is extruded and then sintered. The gasoline fraction typically consists of paraffinic, naphthenic and aromatic hydrocarbons. It is characterized by a special boiling range between 80 and 110 degrees Celsius.

In accordance with an important feature of the invention, the aromatic and olefinic constituents are removed from the special gasoline fraction before the PTFE paste is mixed. In a practical embodiment of the invention, approximately 3 liters of gasoline fraction are rapidly mixed with 150 ml chlorosulphuric acid under agitation. The mixture turns a black colour within a few seconds and black precipitations are formed on the walls of the flask. These precipitations consist essentially of polymers. The mixture is heated under reflux condensation and agitation for approximately one hour.

After cooling, approximately 300–500 ml water is added to the mixture under agitation and the phases are separated. The organic phase is washed with 300–500 ml 1N sodium hydroxide solution and water. After drying over 100–200 g sodium sulphate for approximately 20 minutes and filtration, the mixture is distilled over a packed column. There is little residue. The yield is approximately 85%.

The PTFE tube is then manufactured in the initially mentioned manner using the gasoline fraction purified as described above. The tubes manufactured in this way are substantially free from contamination which might interfere with measurements in an analytical measuring device. They may be used without restriction, for instance in on-line degassers.

When the gasoline fraction is cleaned with chlorosulphuric acid, the acid sulphonates the aromatic compounds, polymerizes the olefins and generally adds to the unsaturated aliphates. Consequently, these substances become non-readily volatile and even water-soluble so that they can be separated out by phase separation or distillation. The chlorosulphuric acid is characterized by a high reactivity towards unsaturated substances and aromatic compounds.

Catalytic hydration may be considered as a possible alternative method of cleaning the gasoline fraction instead of the use of chlorosulphuric acid in accordance with the preferred example embodiment described above.

The present invention is particularly advantageous in gradient elution liquid chromatography. In gradient elution, the concentration of the mobile phase (solvent) is continually changed during the chromatographic procedure. In the current state of the art, the contamination, which is released from PTFE tubings into the mobile phase, for example, is concentrated during gradient elution at the head of the separating column and elutes at corresponding eluent ratios during the gradient. Consequently, a relatively high concentration of impurities, for example UV-absorbing aromatic substances, enter the detector, a UV absorption detector, for instance, and interfere with the measurement there.

DETAILED DESCRIPTION OF DRAWING

The FIGURE illustrates this situation using a typical chromatogram. The chromatogram labelled with the reference numeral 1 in the FIGURE corresponds to the state of the art and was obtained from a chromatograph fitted with a vacuum degasser with conventional PTFE tubes. The chromatogram referenced with numeral 2 illustrates the progress obtained by the present invention. A vacuum degasser with PTFE tubes manufactured in accordance with the invention was used in the generation of chromatogram 2. Both chromatograms were obtained using an acetonitrile-water mixture in gradient operation. A C-18 reversed phase column was used. A UV absorption detector at a wavelength of 210 nm was used as the detector.

The FIGURE clearly shows that PTFE manufactured in the conventional manner causes heavy contamination (chromatogram 1) which fake sample substances that are not present or overlay the actual sample substances. This leads to errors in the quantitative determination of small sample quantities, particularly in trace analysis. Chromatogram 2, by contrast, has a substantially flat pattern, so that no noticeable interference with the quantitative measurement of a sample occurs where plastic parts in accordance with the invention are used.

The invention is not restricted to the manufacture of PTFE parts. Examples of other plastics for which the cleaning method described may be used are FEP (fluorinated ethylene propylene), ETFE (ethylene tetrafluoroethylene), PFA and other polymers containing fluorine. The cleaning method can also be used for other liquids in addition to gasoline fraction, for example, for liquids of aliphatic hydrocarbons.

The embodiment above was described in conjunction with a UV absorption detector. Aromatic contamination is particularly noticeable as an interfering agent there. However, the invention may also be advantageously used in conjunction with fluorescence detectors, for example, since distortion of the measuring result is also prevented on these devices if aromatic contamination is prevented in the mobile phase.

We claim:
1. Method for the manufacture of plastic parts which contact liquids for use in an analytical measuring device, comprising the steps of
    (a) removing a substance selected from the group consisting of aromatic and olefinic substances from a suspension liquid,
    (b) adding said suspension liquid to plastic base material to create a mixture and
    (c) extruding said mixture to form a plastic part.
2. Method in accordance with claim 1, wherein said aromatic and olefinic substances are removed from the suspension liquid by means of a chemical reaction.
3. Method in accordance with claim 2, wherein removal of said substances is effected by the addition of chlorosulphuric acid to the suspension liquid.
4. Method in accordance with claim 1, wherein the plastic part is a tube or a membrane.
5. Method in accordance with claim 1, wherein the plastic base material is polytetrafluoroethylene and the suspension liquid is a gasoline fraction.
6. Plastic part for use in an analytical measuring device coming into contact with the liquids in the measuring device and manufactured in accordance with claim 1.
7. A plastic part manufactured in accordance with claim 1, wherein said plastic part is used in a degasser in an analytical measuring device.
8. Method in accordance with claim 2, wherein the plastic part is a tube or a membrane.
9. Method in accordance with claim 3, wherein the plastic part is a tube or a membrane.
10. Method in accordance with claim 2, wherein the plastic base material is polytetrafluoroethylene and the suspension liquid is a gasoline fraction.
11. Method in accordance with claim 3, wherein the plastic base material is polytetrafluoroethylene and the suspension liquid is a gasoline fraction.
12. Method in accordance with claim 4, wherein the plastic base material is polytetrafluoroethylene and the suspension liquid is a gasoline fraction.
13. Plastic part for use in an analytical measuring device coming into contact with the liquids in the measuring device and manufactured in accordance with claim 2.
14. Plastic part for use in an analytical measuring device coming into contact with the liquids in the measuring device and manufactured in accordance with claim 3.
15. Plastic part for use in an analytical measuring device coming into contact with the liquids in the measuring device and manufactured in accordance with claim 4.
16. Plastic part for use in an analytical measuring device coming into contact with the liquids in the measuring device and manufactured in accordance with claim 5.
17. A plastic part manufactured in accordance with claim 2 wherein said part is a degasser in a liquid chromatograph.
18. A plastic part manufactured in accordance with claim 3 wherein said part is a degasser in a liquid chromatograph.
19. A plastic part manufactured in accordance with claim 4 wherein said part is a degasser in a liquid chromatograph.
20. A plastic part manufactured in accordance with claim 5 wherein said part is a degasser in a liquid chromatograph.
21. Method in accordance with claim 1, wherein the aromatic and olefinic substances are contaminants which add an additional absorption signal which interferes with a measuring signal in a liquid chromatograph.

* * * * *